(12) United States Patent
Lan-Hargest et al.

(10) Patent No.: US 7,057,057 B2
(45) Date of Patent: Jun. 6, 2006

(54) HISTONE DEACETYLASE INHIBITORS BASED ON ALPHA-KETOEPOXIDE COMPOUNDS

(75) Inventors: Hsuan-Yin Lan-Hargest, Fallston, MD (US); Robert J. Kaufman, St. Louis, MO (US)

(73) Assignee: Errant Gene Therapeutics, LLC, Phoenix, MD (US)

( * ) Notice: Subject to any disclaimer, the term of this patent is extended or adjusted under 35 U.S.C. 154(b) by 267 days.

(21) Appl. No.: 10/442,177

(22) Filed: May 21, 2003

(65) Prior Publication Data

US 2004/0029922 A1 Feb. 12, 2004

Related U.S. Application Data

(60) Provisional application No. 60/382,089, filed on May 22, 2002.

(51) Int. Cl.
C07D 303/32 (2006.01)

(52) U.S. Cl. .................. 549/548; 549/554; 514/475
(58) Field of Classification Search ................ 549/548, 549/554; 514/475
See application file for complete search history.

(56) References Cited

U.S. PATENT DOCUMENTS

| 4,447,627 A | 5/1984 | Näf et al. ............... 549/548 |
| 5,451,689 A | 9/1995 | Matsumoto et al. ....... 549/386 |
| 5,935,773 A | 8/1999 | Hagemann et al. ....... 430/505 |
| 6,147,224 A | 11/2000 | Vuligonda et al. ....... 548/518 |
| 6,201,123 B1 | 3/2001 | Daikai et al. ............. 546/21 |
| 6,262,278 B1 | 7/2001 | Jacobsen et al. .......... 549/230 |

FOREIGN PATENT DOCUMENTS

| JP | 2-279735 | 11/1990 |
| JP | 9-249984 | 9/1997 |
| WO | WO 96/28402 | 9/1996 |
| WO | WO 97/35990 | 10/1997 |
| WO | WO 99/31063 | 6/1999 |

OTHER PUBLICATIONS

Bohlmann et al., Phytochemistry, 21(7), pp. 1679–1691, 1982.*
Pashaev et al, Azerb. Khim. Zh. (1978), (2) 48–52.
Colletti et al., "Design and Synthesis of Histone Deacetylase Inhibitors: The Development of Apicidin Transition State Analogs," Tetrahedron Letters, 41, 2000, 7837–7841.
Collins et al., "Oral Sodium Phenylbutyrate Therapy in Homozygous β Thalassemia: A Clinical Trial," Blood, 85(1), 1995, 43–49.
Denney et al., "Preparation and Reactions of Some Phosphobetaines," J. Org. Chem., 27, 1962, 3404–3408.
Dunn et al., "3–tert–Butyldimethylsilyloxymethyl–2–lithio–2–phenylsulfonyloxirane as a Glycidyl Anion Equivalent; Preparation of Terminal Epoxy Ketones," J. Chem Soc. Perkin Trans. 1 (1992), (21), 2863–70.
Freuhauf et al., "Use of the Extreme Drug Resistance Assay to Evaluate Mechanisms of Resistance in Ovarian Cancer: Taxol Resistance and MDR–1 Expression," Chemosensitivity Testing in Gyneologic Malignancies and Breast Cancer, 19, 1994, 39–52.
Grunstein, "Histoneactylation in chromatin structure and transcription," Nature, 389, 1997, 349–352.
Hoffmann et al., "A non–isotopic assay for histone deacetylase activity," Nucleic Acids Research, 27(9), 1999, 2057–2058.
Kolle et al., "Biochemical Methods for Analysis of Histone Deacetylases," Methods: A Comparison to Methods in Enzymology, 15, 1998, 323–331.
Moser et al., "Measurement of Saturated Very Long Chain Fatty Acids in Plasma," Techniques in Diagnostic Human Biochemical Genetics: A Laboratory Manual, 1991, 177–191.
Panyim et al., "High Resolution Acrylamide Gel Electrophoresis of Histones," Archives of Biochemistry and Biophysics, 130, 1969, 337–346.
Parameswara et al., "One–Step Vilsmeier Route to Some 5–Aryl–3–methyl–2(E), 4(E)–pentadienals and their Oxidation to Penta–dienoic Acids," Synthesis, 1980, 815–818.
Pazin et al., "What's Up and Down with Histone Deacetylation and Transcription?," Cell, 89, 1997, 325–328.
Steffan et al., "Histone deacetylase inhibitors arrest polyglutamine–dependent neurodegeneration in Drosphila," Nature, 413, 2001, 739–743.
Steinberg, "The acetylation state of nuclear proteins could be one key to pathology and treatment," The Scientist, 16 (2), 2002, 34.
Trager et al., "Human Malaria Parasites in Continuous Culture," Science, 193, 1976, 673–675.
Wade et al., "Histone acetylation: chromatin in action," Trends Biochem. Sci., 22, 1997, 128–132.
Watkins et al., "Peroxisomal Fatty Acid β–Oxidation in HepG2 Cells," Archives of Biochemistry and Biophysics, 289 (2), 1991, 329–336.
Wolffe, "Histone Deacetylase: A Regulator of Transcription," Science, 272, 1996, 371–372.

* cited by examiner

Primary Examiner—Ba K. Trinh
(74) Attorney, Agent, or Firm—Steptoe & Johnston LLP

(57) ABSTRACT

Histone deacetylase is a metallo-enzyme with zinc at the active site. Compounds having a zinc-binding moiety, for example, an alpha-ketoepoxide group, such as an alpha-ketothio group, can inhibit histone deacetylase. Histone deacetylase inhibition can repress gene expression, including expression of genes related to tumor suppression. Accordingly, inhibition of histone deacetylase can provide an alternate route for treating cancer, hematological disorders, e.g., hemoglobinopathies, autosomal dominant disorders, e.g. spinal muscular atrophy and Huntington's disease, genetic related metabolic disorders, e.g., cystic fibrosis and adrenoleukodystrophy, or to stimulate hematopoietic cells ex vivo.

28 Claims, No Drawings

HISTONE DEACETYLASE INHIBITORS BASED ON ALPHA-KETOEPOXIDE COMPOUNDS

CLAIM OF PRIORITY

This application claims priority under 35 USC §119(e) to U.S. Pat. application Ser. No. 60/382,089, filed on May 22, 2002, the entire contents of which is hereby incorporated by reference.

TECHNICAL FIELD

This invention relates to alpha-ketoepoxide compounds, and more particularly to alpha-ketoepoxide compounds that are histone deacetylase inhibitors.

BACKGROUND

DNA in the nucleus of the cell exists as a hierarchy of compacted chromatin structures. The basic repeating unit in chromatin is the nucleosome. The nucleosome consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function and ultimately gene expression. The covalent modification of histones, such as acetylation, occurs by enzymatically mediated processes.

Regulation of gene expression through the inhibition of the nuclear enzyme histone deacetylase (HDAC) is one of several possible regulatory mechanisms whereby chromatin activity can be affected. The dynamic homeostasis of the nuclear acetylation of histones can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. Histone acetylation can activate DNA transcription, enhancing gene expression. Histone deacetylase can reverse the process and can serve to repress gene expression. See, for example, Grunstein, *Nature* 389, 349–352 (1997); Pazin et al., *Cell* 89, 325–328 (1997); Wade et al., *Trends Biochem. Sci.* 22, 128–132 (1997); and Wolffe, *Science* 272, 371–372 (1996).

SUMMARY

Histone deacetylase is a metallo-enzyme with zinc at the active site. Compounds having a zinc-binding moiety, for example, an alpha-ketoepoxide group, can inhibit histone deacetylase. Histone deacetylase inhibition can alter gene expression, including expression of genes related to tumor suppression. Accordingly, inhibition of histone deacetylase can provide an alternate route for treating cancer, hematological disorders, e.g., hemoglobinopathies, genetic related metabolic disorders, e.g., cystic fibrosis and adrenoleukodystrophy, autosomal dominant disorders, e.g. Huntington's disease and spinal muscular atrophy, and to stimulate hematopoietic cells ex vivo.

In one aspect, a method of inhibiting histone deacetylation activity in cells includes contacting the cells with an effective amount of a compound containing an alpha-ketoepoxide group, wherein the compound is not trapoxin, thereby treating one or more disorders mediated by histone deacetylase to stimulate hematopoietic cells ex vivo, and determining whether the level of acetylated histones in the treated cells is higher than in untreated cells under the same conditions. In the method, the compound can be a compound of formula (I), provided that when each of $Y^1$ and $Y^2$, independently, is a bond or $CH_2$, A is unsubstituted phenyl or heterocyclyl, and L is $C_{4-6}$, L has at least one double bond or at least one triple bond. In the method, the compound can be 1-oxiranyl-8-phenyl-1-octanone, 1-oxiranyl-7-phenyl-2,4,6-heptatrien-1-one, or 1-oxiranyl-7-phenoxy-2,4,6-heptatrien-1-one.

A compound has the formula (I):

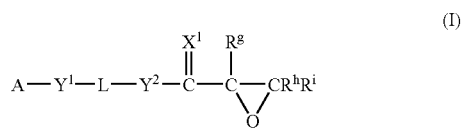

In formula (I), A is a cyclic moiety selected from the group consisting of $C_{3-14}$ cycloalkyl, 3–14 membered heterocycloalkyl, $C_{4-14}$ cycloalkenyl, 3–8 membered heterocycloalkenyl, aryl, or heteroaryl. The cyclic moiety can be optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl. Alternatively, A is a saturated branched $C_{3-12}$ hydrocarbon chain or an unsaturated branched $C_{3-12}$ hydrocarbon chain optionally interrupted by —O—, —S—, —N($R^a$)—, —C(O)—, -N($R^a$)—SO$_2$—, —SO$_2$—N(Ra$^a$)—, —N($R^a$)—C(O)—O—, —O—C(O)—N($R^a$)—, —N($R^a$)—C(O)—N($R^b$)—, —O—C(O)—, —C(O)—O—, —O—SO$_2$—, —SO$_2$—O—, or —O—C(O)—O—. Each of $R^a$ and $R^b$, independently, can be hydrogen, alkyl, alkenyl, alkynyl, alkoxy, hydroxylalkyl, hydroxyl, or haloalkyl. Each of the saturated and the unsaturated branched hydrocarbon chain can be optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl.

In formula (I), each of $Y^1$ and $Y^2$, independently, is —CH$_2$—, —O—, —S—, —N($R^c$)—, —N($R^e$)—, —O—C(O)—O—, —N($R^c$)—, —O—C(O)—N($R^c$)—, —N($R^c$)—C(O)—N($R^d$)—, —C(O)—, —C(N$R^c$), —O—C(O)—O—, or a bond. Each of $R^c$ and $R^d$, independently, can be hydrogen, alkyl, alkenyl, alkynyl, alkoxy, hydroxylalkyl, hydroxyl, or haloalkyl.

In formula (I), L is a straight $C_{4-12}$ hydrocarbon chain optionally containing at least one double bond, at least one triple bond, or at least one double bond and one triple bond. The hydrocarbon chain can be optionally substituted with $C_{1-4}$ alkyl, $C_{2-4}$ alkenyl, $C_{2-4}$ alkynyl, $C_{1-4}$ alkoxy, hydroxyl, halo, amino, thio, alkylthio, arylthio, aralkylthio, acylthio, nitro, cyano, $C_{3-5}$ cycloalkyl, 3–5 membered heterocycloalkyl, monocyclic aryl, 5–6 membered heteroaryl, $C_{1-4}$ alkylcarbonyloxy, $C_{1-4}$ alkyloxycarbonyl, $C_{1-4}$ alkylcarbonyl, or formyl. The hydrocarbon chain can be optionally interrupted by —O—, —N($R^e$)—, —N($R^e$)—C(O)—O—, —O—C(O)—N($R^e$)—, —N($R^e$)—C(O)—N($R^f$)—, or —O—C(O)—O—. Each of $R^e$ and $R^f$, independently, can be hydrogen, alkyl, alkenyl, alkynyl, alkoxy, hydroxylalkyl, hydroxyl, or haloalkyl.

In formula (I), $X^1$ is O or S, and each of $R^g$, $R^h$, and $R^i$, independently, is hydrogen or $C_{1-6}$ alkyl.

In formula (I), when each of $Y^1$ and $Y^2$, independently, is a bond or $CH_2$, A is unsubstituted phenyl or heterocyclyl, and L is $C_{4-7}$, L has at least one double bond or at least one triple bond. In formula (I), when each of $Y^1$ and $Y^2$ is a bond, A is unsubstituted phenyl, and L is $C_4$, L is not a diene.

In certain circumstances: each of $R^g$, $R^h$, and $R^i$ can be hydrogen; $X^1$ can be O; each of $Y^1$ and $Y^2$, independently, can be —$CH_2$—, —O—, —$N(R^c)$—, or a bond; L can be a $C_{4-12}$ hydrocarbon chain; a $C_{5-12}$ hydrocarbon chain, a $C_{5-10}$ hydrocarbon chain, or a $C_{6-8}$ hydrocarbon chain; L can be optionally substituted with $C_{1-2}$ alkyl, $C_{1-2}$ alkoxy, hydroxyl, —$NH_2$, —$NH(C_{1-2}$ alkyl), or —$N(C_{1-2}$ alkyl)$_2$; L can contain at least one double bond, at least one triple bond, or at least one double bond and one triple bond; L can be an unsaturated hydrocarbon chain containing at least one double bond; the double bond can be in trans configuration; L can be an unsaturated hydrocarbon chain containing at least two double bonds; or A is a $C_{5-8}$ cycloalkenyl, 5–8 membered heteroalkenyl, phenyl, naphthyl, indanyl, or tetrahydronaphthyl optionally substituted with alkyl alkenyl, alkynyl, alkoxy, hydroxyl, hydroxylalkyl, halo, haloalkyl, or amino.

In formula (I), the compound can be 1-oxiranyl-7-phenyl-2,4,6-heptatrien-1-one, or 1-oxiranyl-7-phenoxy-2,4,6-heptatrien-1-one.

In certain circumstances, A is phenyl, $Y^1$ is a bond, and L is a $C_{6-12}$ hydrocarbon chain containing three double bonds and the carbon adjacent to $Y^1$ is substituted with phenyl. In other circumstances, A is phenyl, $Y^1$ is a bond, and L is a $C_{3-12}$ hydrocarbon chain and the carbon adjacent to $Y^1$ is substituted with two phenyls.

A salt of any of the compounds can be prepared. For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, and maleate. A compound of this invention may also form a pharmaceutically acceptable salt when a compound of this invention having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts, or ammonium salts or salts of organic bases such as morpholine, piperidine, pyridine, dimethylamine, or diethylamine salts.

It should be recognized that a compound of the invention can contain chiral carbon atoms. In other words, it may have optical isomers or diastereoisomers.

Alkyl is a straight or branched hydrocarbon chain containing 1 to 10 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

Alkenyl and alkynyl refer to a straight or branched hydrocarbon chain containing 2 to 10 carbon atoms and one or more (preferably, 1–4 or more preferably 1–2) double or triple bonds, respectively. Some examples of alkenyl and alkynyl are allyl, 2-butenyl, 2-pentenyl, 2-hexenyl, 2-butynyl, 2-pentynyl, and 2-hexynyl.

Cycloalkyl is a monocyclic, bicyclic or tricyclic alkyl group containing 3 to 14 carbon atoms. Some examples of cycloalkyl are cyclopropyl, cyclopentyl, cyclohexyl, cycloheptyl, adamantyl, and norbornyl. Heterocycloalkyl is a cycloalkyl group containing at least one heteroatom (e.g., 1–3) such as nitrogen, oxygen, or sulfur. The nitrogen or sulfur may optionally be oxidized and the nitrogen may optionally be quaternized. Examples of heterocycloalkyl include piperidinyl, piperazinyl, tetrahydropyranyl, tetrahydrofuryl, and morpholinyl. Cycloalkenyl is a cycloalkyl group containing at least one (e.g., 1–3) double bond. Examples of such a group include cyclopentenyl, 1,4-cyclohexa-di-enyl, cycloheptenyl, and cyclooctenyl groups. By the same token, heterocycloalkenyl is a cycloalkenyl group containing at least one heteroatom selected from the group of oxygen, nitrogen or sulfur.

Aryl is an aromatic group containing a 5–14 member ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1–3) heteroatom such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

The cyclic moiety can be a fused ring formed from two or more of the just-mentioned groups. Examples of a cyclic moiety having fused rings include fluorenyl, dihydro-dibenzoazepine, dibenzocycloheptenyl, 7H-pyrazino[2,3-c]carbazole, or 9,10-dihydro-9,10-[2]buteno-anthracene.

Amino protecting groups and hydroxy protecting groups are well-known to those in the art. In general, the species of protecting group is not critical, provided that it is stable to the conditions of any subsequent reaction(s) on other positions of the compound and can be removed without adversely affecting the remainder of the molecule. In addition, a protecting group may be substituted for another after substantive synthetic transformations are complete. Examples of an amino protecting group include, but not limited to, carbamates such as 2,2,2-trichloroethylcarbamate or tertbutylcarbamate. Examples of a hydroxyl protecting group include, but not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other protecting groups and reaction conditions can be found in T. W. Greene, *Protective Groups in Organic Synthesis*, (3rd, 1999, John Wiley & Sons, New York, N.Y.).

Note that an amino group can be unsubstituted (i.e., —$NH_2$), mono-substituted (i.e., —NHR), or di-substituted (i.e., —$NR_2$). It can be substituted with groups (R) such as alkyl, cycloalkyl, heterocycloalkyl, aryl, heteroaryl, aralkyl, or heteroaralkyl. Halo refers to fluoro, chloro, bromo, or iodo.

Inhibition of a histone deacetylase in a cell is determined by measuring the level of acetylated histones in the treated cells and measuring the level of acetylated histones in untreated cells and comparing the levels. If the level of histone acetylation in the treated cells increases relative to the untreated cells, histone deacetylase has been inhibited.

Some disorders or physiological conditions may be mediated by hyperactive histone deacetylase activity. A disorder or physiological condition that is mediated by histone deacetylase refers to a disorder or condition wherein histone deacetylase plays a role in triggering the onset thereof. Examples of such disorders or conditions include, but not limited to, cancer, hemoglobinopathies (e.g., thalassemia or sickle cell anemia), cystic fibrosis, protozoan infection, spinal muscular atrophy, Huntington's disease, alpha-1 antitrypsin, retrovirus gene vector reactivation, wound healing, hair growth, peroxisome biogenesis disorder, and adrenoleukodystrophy.

Other features or advantages will be apparent from the following detailed description of several embodiments, and also from the appended claims.

DETAILED DESCRIPTION

The compounds of formula (I) and (II) can generally be prepared according to the following methods. Specifically, an alpha-ketoepoxide can be made by dropwise addition of sodium hydroxide to an aldehyde and 1,2-epoxy-3-butanone at a controlled pH of 8.5–9, as shown in Scheme A.

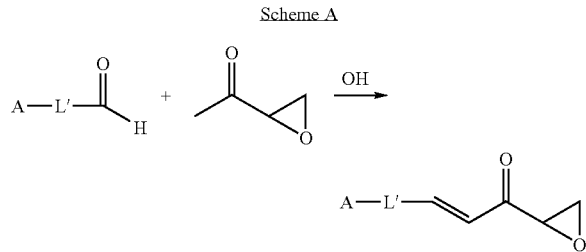

Alternatively, as shown in Scheme B, an alpha-ketoepoxide can be prepared by converting a carboxylic acid to the corresponding Weinreb amide using oxalyl chloride followed by N,O-dimethylhydroxylamine. Subsequently, the Weinreb amide is treated with vinyl Grignard. The resulting vinyl ketone is oxidized with, for example, with m-chloroperbenzoic acid (mCPBA) or an epoxidation catalyst such as Jacobsen's catalyst, to gives the desired alpha-ketoepoxide.

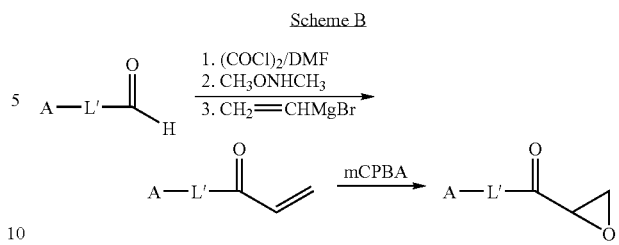

An aldehyde or carboxylic acid-containing compound can be prepared by any known methods in the art. For example, a compound having an unsaturated hydrocarbon chain between A and —$C(=X^1)$— can be prepared according to scheme C:

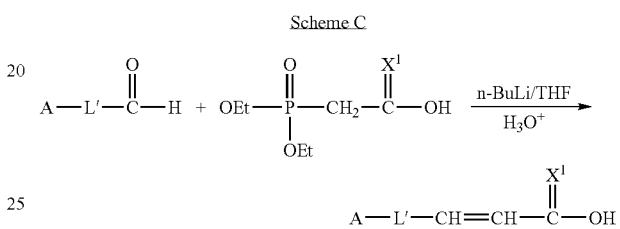

where L' is a saturated or unsaturated hydrocarbon linker between A and —CH=CH— in a compound of the invention, and A and $X^1$ has the same meaning as defined above. See Coutrot et al., *Syn. Comm.* 133–134 (1978). Briefly, butyllithium is added to an appropriate amount of anhydrous tetrahydrofuran (THF) at a very low temperature (e.g., −65° C.). A second solution having diethylphosphonoacetic acid in anhydrous THF is added dropwise to the stirred butyllithium solution at the same low temperature. The resulting solution is stirred at the same temperature for an additional 30–45 minutes which is followed by the addition of a solution containing an aromatic acrylaldehyde in anhydrous THF over 1–2 hours. The reaction mixture is then warmed to room temperature and stirred overnight. It is then acidified (e.g., with HCl) which allows the organic phase to be separated. The organic phase is then dried, concentrated, and purified (e.g., by recrystallization) to form an unsaturated carboxylic acid.

Alternatively, a carboxylic acid-containing compound can be prepared by reacting an acid ester of the formula A-L'—C(=O)—O-lower alkyl with a Grignard reagent (e.g., methyl magnesium iodide) and a phosphorus oxychloride to form a corresponding aldehyde, which can be further oxidized (e.g., by reacting with silver nitrate and aqueous NaOH) to form an unsaturated carboxylic acid.

Other types of carboxylic acid-containing compounds (e.g., those containing a linker with multiple double bonds or triple bonds) can be prepared according to published procedures such as those described, for example, in Parameswara et al., *Synthesis*, 815–818 (1980) and Denny et al., *J. Org. Chem.*, 27, 3404 (1962). As to compounds wherein $X^1$ is S, they can be prepared according to procedures described in Sandler, S. R. and Karo, W., *Organic Functional Group Preparations, Volume III* (Academic Press, 1972) at pages 436–437. Additional synthetic methods can be found in March, *J. Advanced Organic Chemistry*, $4^{th}$ ed., (Wiley Interscience, 1992).

Note that appropriate protecting groups may be needed to avoid forming side products during the preparation of a compound of the invention. For example, if the linker L' contains an amino substituent, it can be first protected by a suitable amino protecting group such as trifluoroacetyl or tert-butoxycarbonyl prior to being treated with reagents such as butyllithium. See, e.g., T. W. Greene, supra, for other suitable protecting groups.

A compound produced by the methods shown above can be purified by flash column chromatography, preparative high performance liquid chromatography, or crystallization.

A pharmaceutical composition including the compound described above can be used to inhibit histone deacetylase in cells and can be used to treat disorders associated with abnormal histone deacetylase activity. Some examples of these disorders are cancers (e.g., leukemia, lung cancer, colon cancer, CNS cancer, melanoma, ovarian cancer, cervical cancer, renal cancer, prostate cancer, and breast cancer), hematological disorders (e.g., hemoglobinopathies, thalassemia, and sickle cell anemia) and genetic related metabolic disorders (e.g., cystic fibrosis, spinal muscular atrophy, peroxisome biogenesis disorder, alpha-1 antitrypsin, and adrenoleukodystrophy). The compounds described above can also stimulate hematopoietic cells ex vivo, ameliorating protozoal parasitic infection, accelerate wound healing, and protecting hair follicles.

An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.* 50, 219 (1966). Body surface area may be approximately determined from height and weight of the patient. See, e.g., *Scientific Tables*, Geigy Pharmaceuticals, Ardsley, N.Y., 537 (1970). An effective amount of a compound described herein can range from about 1 mg/kg to about 300 mg/kg. Effective doses will also vary, as recognized by those skilled in the art, dependent on route of administration, excipient usage, and the possibility of co-usage, pre-treatment, or post-treatment, with other therapeutic treatments including use of other chemotherapeutic agents and radiation therapy. Other chemotherapeutic agents that can be co-administered (either simultaneously or sequentially) include, but not limited to, paclitaxel and its derivatives (e.g., taxotere), doxorubicin, L-asparaginase, dacarbazine, amascrine, procarbazine, hexamethylmelamine, mitoxantrone, and gemicitabine.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. Because some of the compounds described herein can have limited water solubility, a solubilizing agent can be included in the composition to improve the solubility of the compound. For example, the compounds can be solubilized in polyethoxylated castor oil (Cremophor EL®) and may further contain other solvents, e.g., ethanol. Furthermore, compounds described herein can also be entrapped in liposomes that may contain tumor-directing agents (e.g., monoclonal antibodies having affinity towards tumor cells).

A compound described herein can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound described herein with a solid carrier and a lubricant. Examples of solid carriers include starch and sugar bentonite. Compounds of this invention can also be administered in a form of a hard shell tablet or a capsule containing a binder, e.g., lactose or mannitol, a conventional filler, and a tableting agent.

The activities of a compound described herein can be evaluated by methods known in the art, e.g., MTT (3-[4,5-dimehtythiazol-2-yl]-2,5-diphenyltrazolium bromide) assay, clonogenic assay, ATP assay, or Extreme Drug Resistance (EDR) assay. See Freuhauf, J. P. and Manetta, A., *Chemosensitivity Testing in Gynecologic Malignancies and Breast Cancer* 19, 39–52 (1994). The EDR assay, in particular, is useful for evaluating the antitumor and antiproliferative activity of a compound described herein. Cells are treated for four days with a compound. Both untreated and treated cells are pulsed with tritiated thymidine for 24 hours. Radioactivity of each type of cells is then measured and compared. The results are then plotted to generate drug response curves, which allow $IC_{50}$ values (the concentration of a compound required to inhibit 50% of the population of the treated cells) to be determined.

Histone deacetylase inhibitory activity can be measured based on procedures described by Hoffmann et al., *Nucleic Acids Res.*, 27, 2057–2058 (1999). Briefly, the assay starts with incubating the isolated histone deacetylase enzyme with a compound of the invention, followed by the addition of a fluorescent-labeled lysine substrate (contains an amino group at the side chain which is available for acetylation). HPLC is used to monitor the labeled substrate. The range of activity of each test compound is preliminarily determined using results obtained from HPLC analyses. $IC_{50}$ values can then be determined from HPLC results using different concentrations of compounds of this invention. All assays are duplicated or triplicated for accuracy. The histone deacetylase inhibitory activity can be compared with the increased activity of acetylated histone for confirmation.

Compounds of this invention are also evaluated for effects on treating X-linked adrenoleukodystrophy (X-ALD), a peroxisomal disorder with impaired very long-chain fatty acid (VLCFA) metabolism. In such an assay, cell lines derived from human primary fibroblasts and (EBV-transformed lymphocytes) derived from X-ALD patients grown on RPMI are employed. Tissue culture cells are grown in the presence or absence of test compounds. For VLCFA measurements, total lipids are extracted, converted to methyl esters, purified by TLC and subjected to capillary GC analysis as described in Moser et al., *Technique in Diagnostic Biochemical Genetics: A Laboratory Manual* (ed A., H. F.) 177–191 (Wiley-Liss, New York, 1991). C24:0 β-oxidation activity of lymphoclastoid cells are determined by measuring their capacity to degrade $[1-^{14}C]$—C24:0 fatty acid to water-soluble products as described in Watkins et al., *Arch. Biochem. Biophys.* 289, 329–336 (1991). The statistical significance of measured biochemical differences between untreated and treated X-ALD cells can be determined by a two-tailed Student's t-test.

Further, compounds of the present invention are evaluated for their effects in treating cystic fibrosis (CF). Since the initial defect in the majority of cases of CF is the inability of mutant CF protein (CFTR) to fold properly and exit the ER, compounds of the invention are tested to evaluate their efficacy in increasing the trafficking of the CF protein out of the ER and its maturation through the Golgi. During its biosynthesis, CFTR is initially synthesized as a nascent polypeptide chain in the rough ER, with a molecular weight of around 120 kDa (Band A). It rapidly receives a core glycosylation in the ER, giving it a molecular weight of around 140 kDa (Band B). As CFTR exits the ER and matures through the Golgi stacks, its glycosylation is modified until it achieves a terminal mature glycosylation, affording it a molecular weight of around 170 kDa (Band C). Thus, the extent to which CFTR exits the ER and traverses the Golgi to reach the plasma membrane may be reflected in the ratio of Band B to Band C protein. CFTR is immunoprecipitated from control cells, and cells exposed to test compounds. Both wt CFTR and ΔF508 CFTR expressing cells are tested. Following lysis, CFTR are immunoprecipitated using various CFTR antibodies. Immunoprecipitates are then subjected to in vitro phosphorylation using radioactive ATP and exogenous protein kinase A. Samples are subsequently solubilized and resolved by SDS-PAGE. Gels are then dried and subject to autoradiography and phosphor image analysis for quantitation of Bands B and C are determined on a BioRad personal fix image station.

Furthermore, compounds of this invention can be used to treat homozygous β thalassemia, a disease in which there is inadequate production of β globin leading to severe anemia. See Collins et al., *Blood,* 85(1), 43–49 (1995).

Still further, compounds of the present invention are evaluated for their use as antiprotozoal or antiparasitic agents. The evaluation can be conducted using parasite cultures (e.g., Asexual *P. falciparum*). See Trager, W. & Jensen, J. B., *Science* 193, 673–675 (1976). Test compounds are dissolved in dimethyl sulfoxide (DMSO) and added to wells of a flat-bottomed 96-well microtitre plate containing human serum. Parasite cultures are then added to the wells, whereas control wells only contain parasite cultures and no test compound. After at least one invasion cycle, and addition of labeled hypoxanthine monohydrochloride, the level of incorporation of labeled hypoxanthine is detected. $IC_{50}$ values can be calculated from data using a non-linear regression analysis.

The toxicity of a compound described herein is evaluated when a compound of the invention is administered by single intraperitoneal dose to test mice. After administration of a predetermined dose to three groups of test mice and untreated controls, mortality/morbidity checks are made daily. Body weight and gross necropsy findings are also monitored. For reference, see Gad, S. C. (ed.), *Safety Assessment for Pharmaceuticals* (Van Nostrand Reinhold, New York, 1995).

The following specific examples, which described syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

EXAMPLES

Synthesis of 5-phenyl-2,4-pentadienal

To a cooled (0–5 ° C.) 927 mL of 1 M solution of phenyl magnesium bromide in tetrahydrofuran was added dropwise a solution of crotonaldehyde (65.0 g) in 130 mL of anhydrous ether over a period of 2 hours and 45 minutes. The reaction was stirred for an additional 45 minutes and then warmed to room temperature. After four more hours of stirring, saturated ammonium chloride aqueous solution (750 mL) was added to the reaction. The mixture was extracted with 750 mL of ether twice. The combined extract was dried over anhydrous potassium carbonate and filtered. The solvent was evaporated to give 135.88 g (99.9%) of the desired 1-phenyl-2-buten-1-ol as an oil which was used in the next step without further purification.

1-Phenyl-2-buten-1-ol (135.88 g) was dissolved in 2300 mL of dioxane and treated with 2750 mL of dilute hydrochloric acid (2.3 mL of concentrated hydrochloric acid in 2750 mL of water) at room temperature. The mixture was stirred overnight and then poured into 4333 mL of ether and neutralized with 2265 mL of saturated aqueous sodium bicarbonate. The aqueous phase was extracted with 1970 mL of ether. The combined extract was dried over anhydrous potassium carbonate. Evaporation of the solvent followed by Kugelrohr distillation at 30° C. for 30 minutes afforded 131.73 g (96.8%) of the desired 4-phenyl-3-buten-2-ol as an oil which was used in the next step without further purification.

Dimethylformamide (DMF, anhydrous, 14 mL) was cooled to 0–5 ° C. and phosphorus oxychloride (8.2 mL) was added dropwise over a period of 40 minutes. The resulting solution was added dropwise to a cooled (0–5° C.) solution of 4-phenyl-3-buten-2-ol (10 g) in 32 mL of anhydrous DMF over a period of an hour. The reaction mixture was warmed to room temperature over a 35-minute period and then gradually heated up to 80° C. over a period of 45 minutes. The reaction was stirred at 80° C. for three hours and then cooled to 0–5° C. To the cooled reaction solution was added dropwise a solution of sodium acetate (40 g) in deionized water (100 mL) over a period of one hour. The mixture was then reheated to 80° C., stirred at 80° C. for an additional 10 minutes, cooled down to room temperature and extracted with ether (100 mL) twice. The combined extract was washed with brine (100 mL), dried over anhydrous sodium sulfate, filtered and concentrated under vacuum to yield 8.78 g of the desired 5-phenyl-2,4-pentadienal as a liquid which was used in the next step without further purification. $^1$H NMR (CDCl$_3$, 300 MHz), δ(ppm) 7.51 (m, 2 H), 7.37 (m, 3 H), 7.26 (m, 1 H), 7.01 (m, 2 H), 6.26 (m, 1 H). The synthesis is summarized in Scheme I.

Scheme I

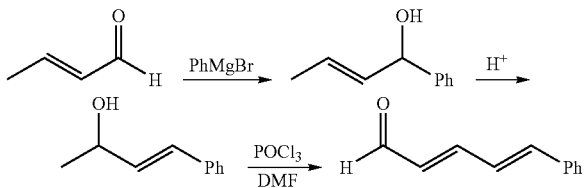

Synthesis of 5-phenoxy-2,4-pentadienal

2-Formylvinyl phenyl ether is prepared by treating phenoxyacetaldehyde with formaldehyde and diethylamine hydrochloride salt. The ether is then reacting with a solution of diethylphosphonoacetic acid and n-butyllithium in anhydrous tetrahydrofuran (THF) to form 5-phenoxy-2,4-pentadienoic acid. 5-Phenyl-2,4-pentadienal is obtained by first converting the carboxylic acid to a Weinreb amide using oxalyl chloride followed by N,O-dimethylhydroxylamine. Subsequently, reduction of the Weinreb amide with lithium aluminum hydride (LAH) in THF leads to the formation of 5-phenoxy-2,4-pentadienal. The synthesis is summarized in Scheme II.

Scheme II

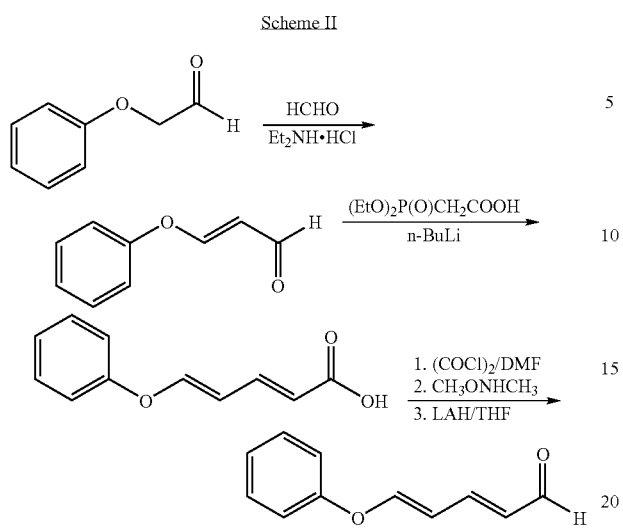

Synthesis of 1,2-epoxy-3-butanone 1,2-Epoxy-3-butanone was prepared by treating methyl vinyl ketone in methanol with 30% of hydrogen peroxide followed by 10% aqueous sodium hydroxide, as shown below.

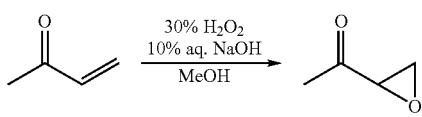

Synthesis of 1-oxiranyl-7-phenyl-2,4,6-heptatrien-1-one

1-Oxiranyl-7-phenyl-2,4,6-heptatrien-1-one is made by dropwise addition of 5% aqueous sodium hydroxide to a mixture of 5-phenyl-2,4-pentadienal and 1,2-epoxy-3-butanone at a controlled pH of 8.5–9, as shown in Scheme IIIA.

Scheme IIIA

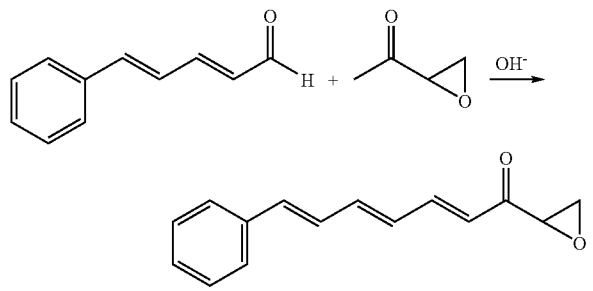

Alternatively, as shown in Scheme IV, 1-oxiranyl-7-phenyl-2,4,6-heptatrien-1-one can be prepared by converting 7-phenyl-2,4,6-heptatrienoic acid to the corresponding Weinreb amide using oxalyl chloride followed by N,O-dimethylhydroxylamine. Subsequently, oxidation of the Weinreb amide with m-chloroperbenzoic acid (mCPBA) gives the desired alpha-keto epoxide.

Scheme IV

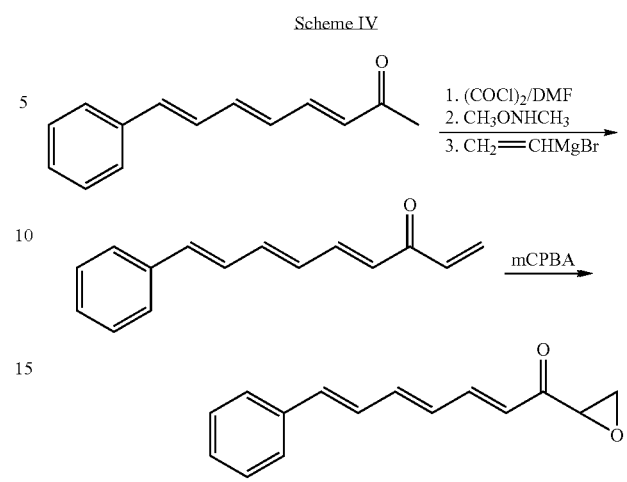

Synthesis of 1-Oxiranyl-7-phenoxy-2,4,6-heptatrien-1-one

1-Oxiranyl-7-phenoxy-2,4,6-heptatrien-1-one is made by dropwise addition of 5% aqueous sodium hydroxide to a mixture of 5-phenoxy-2,4-pentadienal and 1,2-epoxy-3-butanone at a controlled pH of 8.5–9, as shown in Scheme IIIB.

Scheme IIIB

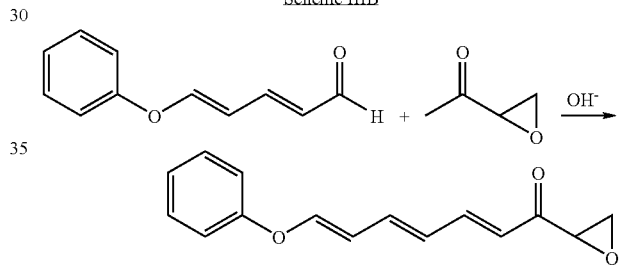

Assays

Compounds selected from 1-oxiranyl-8-phenyl-1-octanone (prepared according to the procedure described in Bioorg. & Med. Chem. Lett., 9 (1999), 2283–2288), 1-oxiranyl-7-phenyl-2,4,6-heptatrien-1-one, or 1-oxiranyl-7-phenoxy-2,4,6-heptatrien-1-one are used in the assays described below.

In vitro Efficacy Studies—Extreme Drug Resistance (EDR) Assay

The PC3 cell line is maintained in RPMI supplemented with 10% fetal calf serum and antibiotics. Cells are suspended in 0.12% soft agar in complete medium and plated (2,000 cells per well) in different drug concentrations onto a 0.4% agarose underlayer in 24-well plates. Plating calls on agarose underlayers supports the proliferation only of the transformed cells, ensuring that the growth signal stems from the malignant component of the tumor.

All compounds are dissolved in DMSO to 200x stock solutions. Stock solutions are diluted to 20x working solutions using the tissue culture medium, then are serially diluted and added to the 24-well plates. The initial range of concentrations is 1 micromolar to 200 micromolar. No significant changes in pH of the culture medium are observed under the above conditions. Diluent control wells contain PC3 cells treated with DMSO, at the dilutions used for appropriate drug treatment. All experimental points are represented by two separate wells (duplicates). Four wells containing tumor cells that are not treated with drugs serve as negative controls in each experiment.

Cells are incubated with drugs under standard culture conditions for 5 days. Cultures are pulsed with tritiated thymidine ($^3$H-TdR, New Life Science Products, Boston, Mass.) at 5 µCi per well for the last 48 hours of the culture period. Cell culture plates are then heated to 90° C. to liquefy the agarose, and cells are harvested onto glass fiber filters, which are then placed into counting vials containing liquid scintillation fluid. The radioactivity trapped on the filters is counted with a Beckman scintillation counter. The fraction of surviving cells is determined by comparing $^3$H-TdR incorporation in treated (experimental points) and untreated (negative control) wells. Microsoft Excel is used to organize the raw data on EDR experiments, and the SigmaPlot program is utilized to generate drug response curves. All drug response curves are approximated as sigmoidal equations (characteristic for typical drug response curves) to fit the data. IC$_{50}$ values are determined using the approximated sigmoidal curves and expressed as µM.

Histone (Hyper)Acetylation Assay

The effect of a compound described herein on histone acetylation can be evaluated in an assay using mouse erythroleukemia cells. Studies are performed with the DS19 mouse erythroleukemia cells maintained in RPMI 1640 medium with 25 mM HEPES buffer and 5% fetal calf serum. The cells are incubated at 37° C.

Histones are isolated from cells after incubation for periods of 2 and 24 hours. The cells are centrifuged for 5 minutes at 2000 rpm in the Sorvall SS34 rotor and washed once with phosphate buffered saline. The pellets are suspended in 10 mL lysis buffer (10 mM Tris, 50 mM sodium bisulfite, 1% Triton X-100, 10 mM magnesium chloride, 8.6% sucrose, pH 6.5) and homogenized with six strokes of a Teflon pestle. The solution is centrifuged and the pellet washed once with 5 mL of the lysis buffer and once with 5 mL 10 mM Tris, 13 mM EDTA, pH 7.4. The pellets are extracted with 2×1 mL 0.25 N HCl. Histones are precipitated from the combined extracts by the addition of 20 mL acetone and refrigeration overnight. The histones are pelleted by centrifuging at 5000 rpm for 20 minutes in the Sorvall SS34 rotor. The pellets are washed once with 5 mL acetone and protein concentration are quantitated by the Bradford procedure.

Separation of acetylated histones is usually performed with an acetic acid-urea polyacrylamide gel electrophoresis procedure. Resolution of acetylated H4 histones is achieved with 6.25 N urea and no detergent as originally described by Panyim and Chalkley, *Arch. Biochem. Biophys.* 130, 337–346 (1969). 25 µg Total histones are applied to a slab gel which is run at 20 mA. The run is continued for a further two hours after the Pyronin Y tracking dye has run off the gel. The gel is stained with Coomassie Blue R. The most rapidly migrating protein band is the unacetylated H4 histone followed by bands with 1, 2, 3 and 4 acetyl groups which can be quantitated by densitometry. The procedure for densitometry involves digital recording using the Alpha Imager 2000, enlargement of the image using the PHOTO-SHOP program (Adobe Corp.) on a MACINTOSH computer (Apple Corp.), creation of a hard copy using a laser printer and densitometry by reflectance using the Shimadzu CS9000U densitometer. The percentage of H4 histone in the various acetylated states is expressed as a percentage of the total H4 histone.

The concentration of a compound of the invention required to decrease the unacetylated H4 histone by 50% (i.e., EC$_{50}$) can then be determined from data obtained using different concentrations of test compounds.

Histone Deacetylation Assay

The determination of the inhibition of histone deacetylase by compounds described herein is based upon the procedure described by Hoffmann et al., *Nucleic Acids Res.* 27, 2057–2058 (1999). The histone deacetylase is isolated from rat liver as previously described in Kolle, D. et al. *Methods: A Companion to Methods in Enzymology* 15: 323–331 (1998). Compounds are initially dissolved in either ethanol or in DMSO to provide a working stock solution. The synthetic substrate used in the assay is N-(4-methyl-7-coumarinyl)-N-α(tert-butyloxy-carbonyl)-N-Ω-acetyllysineamide (MAL).

The assay is performed in a final total volume of 120 µL consisting of 100 µL of 15 mM tris-HCl buffer at pH 7.9 and 0.25 mM EDTA, 10 mM NaCl, 10% glycerol, 10 mM mercaptoethanol and the enzyme. The assay is initiated upon the addition of 10 µL of a test compound followed by the addition of a fluorescent-labeled lysine substrate to each assay tube in an ice bath for 15 minutes. The tubes are transferred to a water bath at 37° C. for an additional 90 minutes.

An initial assay is performed to determine the range of activity of each test compound. The determination of IC$_{50}$ values is made from the results of five dilutions in range according to the expected potency for each test compound. Each assay is duplicated or triplicated.

Other embodiments are within the scope of the following claims.

What is claimed is:

1. A compound having the formula (I):

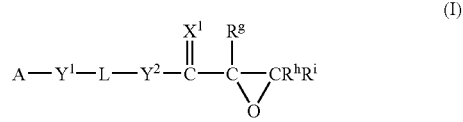

wherein

A is a cyclic moiety selected from the group consisting of C$_{3\text{-}14}$ cycloalkyl, 3–14 membered heterocycloalkyl, C$_{4\text{-}14}$ cycloalkenyl, 3–8 membered heterocycloalkenyl, aryl, and heteroaryl; the cyclic moiety being optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl; or A is a saturated branched C$_{3\text{-}12}$ hydrocarbon chain or an unsaturated branched C$_{3\text{-}12}$ hydrocarbon chain optionally interrupted by —O—, —S—, —N(R$^a$), —C(O)—, —N(R$^a$)—SO$_2$—, —SO$_2$—N(R$^a$), —N(R$^a$)—C(O)—O—, —O—C(O)—N(R$^a$)—, —N(R$^a$)—C(O)—N(R$^b$)—, —O—C(O)—, —C(O)—O—, —O—SO$_2$—, —SO$_2$—O—, or —O—C(O)—O—, where each of R$^a$ and R$^b$ independently, is hydrogen, alkyl, alkenyl, alkynyl, alkoxy, hydroxylalkyl, hydroxyl, or haloalkyl; each of the saturated and the unsaturated branched hydrocarbon chain being optionally substituted with alkyl, alkenyl, alkynyl, alkoxy, hydroxyl, hydroxylalkyl, halo, haloalkyl, amino, thio, alkylthio, arylthio, aralkylthio, acylthio, alkylcarbonyloxy, alkyloxycarbonyl, alkylcarbonyl, alkylsulfonylamino, aminosulfonyl, or alkylsulfonyl;

each of Y$^1$ and Y$^2$, independently, is —CH$_2$—, —O—, —S—, —N(R$^c$)—, —N(R$^c$)—C(O)—O—, —N(R$^c$)—

—C(O)—, —C(O)—N(R$^c$)—, —O—C(O)—N(R$^c$)—, —N(R$^c$)—C(O)—N(R$^d$)—, —C(O)—, —C(NR$^c$)—, —O—C(O)—O—, or a bond; each of R$^c$ and R$^d$, independently, being hydrogen, alkyl, alkenyl, alkynyl, alkoxy, hydroxyalkyl, hydroxyl, or haloalkyl;

L is a straight $C_{4-12}$ hydrocarbon chain optionally containing at least one double bond, at least one triple bond, or at least one double bond and one triple bond; the hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, amino, thio, alkylthio, arylthio, aralkylthio, acylthio, nitro, cyano, $C_{3-5}$ cycloalkyl, 3–5 membered heterocycloalkyl, monocyclic aryl, 5–6 membered heteroaryl, $C_{1-4}$ alkylcarbonyloxy, $C_{1-4}$ alkyloxycarbonyl, $C_{1-4}$ alkylcarbonyl, or formyl; and further being optionally interrupted by —O—, —N(R$^e$)—, —N(R$^e$)—C(O)—O—, —O—C(O)—N (R$^e$)—, —(R$^e$)—C(O)—N(R$^f$)— or —O—C(O)—O—; each of R$^e$ and R$^f$, independently, being hydrogen, alkyl, alkenyl, alkynyl, alkoxy, hydroxyalkyl, hydroxyl, or haloalkyl;

X$^1$ is O or S; and each of R$^g$, R$^h$, and R$^i$, independently, is hydrogen or $C_{1-6}$ alkyl;

provided that when each of Y$^1$ and Y$^2$, independently, is a bond or CH$_2$, A is unsubstituted phenyl or heterocyclyl, and L is $C_{4-7}$, L has at least one double bond or at least one triple bond, and when each of Y$^1$ and Y$^2$ is a bond, A is unsubstituted phenyl, and L is $C_4$, L is not a diene;

or a salt thereof.

2. The compound of claim 1, wherein each of R$^g$, R$^h$, and R$^i$ are hydrogen.

3. The compound of claim 1, wherein X$^1$ is O.

4. The compound of claim 2, wherein X$^1$ is O.

5. The compound of claim 1, wherein each of Y$^1$ and Y$^2$, independently, is —CH$_2$—, —O—, —N(R$^c$)—, or a bond.

6. The compound of claim 4, wherein each of Y$^1$ and Y$^2$, independently, is —CH$_2$—, —O—, —N(R$^c$)—, or a bond.

7. The compound of claim 1, wherein L is a $C_{4-12}$ hydrocarbon chain optionally substituted with $C_{1-2}$ alkyl, $C_{1-2}$ alkoxy, hydroxyl, —NH$_2$, —NH($C_{1-2}$ alkyl), or —NH($C_{1-2}$ alkyl)$_2$.

8. The compound of claim 1, wherein L is a $C_{5-12}$ hydrocarbon chain substituted with $C_{1-2}$ alkyl, $C_{1-2}$ alkoxy, hydroxyl, —NH$_2$, —NH($C_{1-2}$ alkyl), or —N($C_{1-2}$ alkyl)$_2$.

9. The compound of claim 1, wherein L is a $C_{5-10}$ hydrocarbon chain substituted with $C_{1-2}$ alkyl, $C_{1-2}$ alkoxy, hydroxyl, —NH$_2$, —NH($C_{1-2}$ alkyl), or —N($C_{1-2}$ alkyl)$_2$.

10. The compound of claim 1, wherein L is a $C_{6-8}$ hydrocarbon chain substituted with $C_{1-2}$ alkyl, $C_{1-2}$ alkoxy, hydroxyl, —NH$_2$, —NH($C_{1-2}$ alkyl), or —N($C_{1-2}$ alkyl)$_2$.

11. The compound of claim 4, wherein L is a $C_{5-10}$ hydrocarbon chain substituted with $C_{1-2}$ alkyl, $C_{1-2}$ alkoxy, hydroxyl, —NH$_2$, —NH($C_{1-2}$ alkyl), or —N($C_{1-2}$ alkyl)$_2$.

12. The compound of claim 1, wherein L contains at least one double bond, at least one triple bond, or at least one double bond and one triple bond.

13. The compound of claim 4, wherein L contains at least one double bond, at least one triple bond, or at least one double bond and one triple bond.

14. The compound of claim 1, wherein L is an unsaturated hydrocarbon chain containing at least one double bond.

15. The compound of claim 14, wherein the double bond is in the trans configuration.

16. The compound of claim 4, wherein L is an unsaturated hydrocarbon chain containing at least one double bond.

17. The compound of claim 16, wherein the double bond is in the trans configuration.

18. The compound of claim 1, wherein L is an unsaturated hydrocarbon chain containing at least two double bonds.

19. The compound of claim 4, wherein L is an unsaturated hydrocarbon chain containing at least two double bonds.

20. The compound of claim 1, wherein A is a $C_{5-8}$ cycloalkenyl, 5–8 membered heteroalkenyl, phenyl, naphthyl, indanyl, or tetrahydronaphthyl optionally substituted with alkyl alkenyl, alkynyl, alkoxy, hydroxyl, hydroxylalkyl, halo, haloalkyl, or amino.

21. The compound of claim 4, wherein A is a $C_{5-8}$ cycloalkenyl, 5–8 membered heteroalkenyl, phenyl, naphthyl, indanyl, or tetrahydronaphthyl optionally substituted with alkyl alkenyl, alkynyl, alkoxy, hydroxyl, hydroxylalkyl, halo, haloalkyl, or amino.

22. The compound of claim 1, wherein A is a phenyl optionally substituted with alkyl, alkenyl, alkynyl, alkoxy, hydroxyl, hydroxylalkyl, halo, haloalkyl, or amino.

23. The compound of claim 4, wherein A is a phenyl optionally substituted with alkyl, alkenyl, alkynyl, alkoxy, hydroxyl, hydroxylalkyl, halo, haloalkyl, or amino.

24. The compound of claim 1, wherein A is phenyl, Y$^1$ is a bond, and L is a $C_{6-12}$ hydrocarbon chain containing three double bonds and the carbon adjacent to Y$^1$ is substituted with phenyl.

25. The compound of claim 4, wherein A is phenyl, Y$^1$ is a bond, and L is a $C_{6-12}$ hydrocarbon chain containing three double bonds and the carbon adjacent to Y$^1$ is substituted with phenyl.

26. The compound of claim 1, wherein A is phenyl, Y$^1$ is a bond, and L is a $C_{4-12}$ hydrocarbon chain and the carbon adjacent to Y$^1$ is substituted with two phenyl groups.

27. The compound of claim 4, wherein A is phenyl, Y$^1$ is a bond, and L is a $C_{4-12}$ hydrocarbon chain and the carbon adjacent to Y$^1$ is substituted with two phenyl groups.

28. The compound of claim 1, wherein the compound is 1-oxiranyl-7-phenyl-2,4,6-heptatrien-1-one, or 1-oxiranyl-7-phenoxy-2,4,6-heptatrien-1-one.

* * * * *